(12) United States Patent  
Hershkowitz et al.

(10) Patent No.: US 8,455,707 B2
(45) Date of Patent: Jun. 4, 2013

(54) METHANE CONVERSION TO HIGHER HYDROCARBONS

(75) Inventors: Frank Hershkowitz, Liberty Corner, NJ (US); John Scott Buchanan, Lambertville, NJ (US); Harry W. Deckman, Clinton, NJ (US); Jeffrey W. Frederick, Centreville, VA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 463 days.

(21) Appl. No.: 12/886,324

(22) Filed: Sep. 20, 2010

(65) Prior Publication Data

US 2011/0009681 A1 Jan. 13, 2011

Related U.S. Application Data

(60) Division of application No. 11/643,541, filed on Dec. 21, 2006, now Pat. No. 7,943,808, and a continuation-in-part of application No. 11/639,691, filed on Dec. 15, 2006, now Pat. No. 7,846,401.

(60) Provisional application No. 60/753,961, filed on Dec. 23, 2005.

(51) Int. Cl.
*C07C 5/35* (2006.01)
(52) U.S. Cl.
USPC ............ 585/535; 585/536; 422/625; 422/628
(58) Field of Classification Search
USPC .................. 585/535–536, 634; 422/625, 628, 422/630, 638
See application file for complete search history.

(56) References Cited

U.S. PATENT DOCUMENTS

| 1,723,679 | A | 8/1929 | Coberly et al. |
| 1,726,877 | A | 9/1929 | Battig |
| 1,843,965 | A | 2/1932 | Wulff |
| 1,880,306 | A | 10/1932 | Wulff |
| 1,880,307 | A | 10/1932 | Wulff |
| 1,880,308 | A | 10/1932 | Wulff |

(Continued)

FOREIGN PATENT DOCUMENTS

| CA | 306 263 | 12/1930 |
| EP | 0 219 163 | 4/1987 |

(Continued)

OTHER PUBLICATIONS

Annaland, M. et al. *A Novel Reverse Flow Reactor Coupling Endothermic and Exothermic Reactions: An Experimental Study*, Chemical Engineering Science, 2002, vol. 57, pp. 4967-4985.

(Continued)

*Primary Examiner* — Brian McCaig

(57) ABSTRACT

The present invention provides a process for the manufacture of acetylene and other higher hydrocarbons from methane feed using a reverse-flow reactor system, wherein the reactor system includes (i) a first reactor and (ii) a second reactor, the first and second reactors oriented in a series relationship with respect to each other, the process comprising supplying each of first and second reactant through separate channels in the first reactor bed of a reverse-flow reactor such that both of the first and second reactants serve to quench the first reactor bed, without the first and second reactants substantially reacting with each other until reaching the core of the reactor system.

4 Claims, 6 Drawing Sheets

U.S. PATENT DOCUMENTS

| | | | |
|---|---|---|---|
| 1,880,309 A | 10/1932 | Wulff | |
| 1,880,310 A | 10/1932 | Wulff | |
| 1,917,627 A | 7/1933 | Wulff | |
| 1,938,991 A | 12/1933 | Wulff | |
| 1,966,779 A | 7/1934 | Wulff | |
| 1,996,185 A | 4/1935 | Wulff | |
| 2,037,056 A | 4/1936 | Wulff | |
| 2,236,534 A | 4/1941 | Hasche | |
| 2,236,555 A | 4/1941 | Wulff | |
| 2,313,157 A | 3/1943 | Linder | |
| 2,319,679 A | 5/1943 | Hasche et al. | |
| 2,343,866 A | 3/1944 | Hincke | |
| 2,359,759 A | 10/1944 | Hebbard et al. | |
| 2,470,578 A | 5/1949 | Royster | |
| 2,556,835 A | 6/1951 | Barr | |
| 2,558,861 A | 7/1951 | Liggett | |
| 2,580,766 A | 1/1952 | Hall | |
| 2,645,673 A | 7/1953 | Hasche | |
| 2,678,339 A | 5/1954 | Harris | |
| 2,692,819 A | 10/1954 | Hasche et al. | |
| 2,706,210 A | 4/1955 | Harris | |
| 2,718,534 A | 9/1955 | Harris | |
| 2,796,951 A | 6/1957 | Bogart | |
| 2,813,919 A | 11/1957 | Pearce | |
| 2,830,677 A | 4/1958 | Coberly | |
| 2,845,335 A | 7/1958 | Hasche | |
| 2,851,340 A | 9/1958 | Coberly et al. | |
| 2,878,262 A | 3/1959 | Hutchings | |
| 2,885,455 A | 5/1959 | Hennig | |
| 2,886,615 A | 5/1959 | Lindahl | |
| 2,920,123 A | 1/1960 | Oldershaw et al. | |
| 2,921,100 A | 1/1960 | Pettyjohn et al. | |
| 2,956,864 A | 10/1960 | Coberly | |
| 2,967,205 A | 1/1961 | Coberly | |
| 3,024,094 A | 3/1962 | Coberly | |
| 3,093,697 A | 6/1963 | Kasbohm et al. | |
| 3,156,733 A | 11/1964 | Happel et al. | |
| 3,156,734 A | 11/1964 | Happel | |
| 3,796,768 A | 3/1974 | Starzenski et al. | |
| 3,865,927 A | 2/1975 | Watson | |
| 4,176,045 A | 11/1979 | Leftin et al. | |
| 4,200,682 A | 4/1980 | Sederquist | |
| 4,240,805 A | 12/1980 | Sederquist | |
| 4,293,315 A | 10/1981 | Sederquist | |
| 4,443,325 A | 4/1984 | Chen et al. | |
| 4,642,272 A | 2/1987 | Sederquist | |
| 4,751,055 A | 6/1988 | Jubin, Jr. | |
| 4,754,095 A | 6/1988 | Coughenour et al. | |
| 4,816,353 A | 3/1989 | Wertheim et al. | |
| 4,926,001 A | 5/1990 | Alagy et al. | |
| 4,929,789 A | 5/1990 | Gupta et al. | |
| 4,973,777 A | 11/1990 | Alagy et al. | |
| 5,080,872 A | 1/1992 | Jezl et al. | |
| 5,138,113 A | 8/1992 | Juguin et al. | |
| 5,976,352 A | 11/1999 | Busson et al. | |
| 6,027,635 A | 2/2000 | Busson et al. | |
| 6,076,487 A | 6/2000 | Wulff et al. | |
| 6,210,157 B1 | 4/2001 | Kobayashi | |
| 6,287,351 B1 | 9/2001 | Wulff et al. | |
| 6,302,188 B1 | 10/2001 | Ruhl et al. | |
| 6,322,760 B1 | 11/2001 | Busson et al. | |
| 6,575,147 B2 | 6/2003 | Wulff et al. | |
| 6,767,530 B2 | 7/2004 | Kobayashi et al. | |
| 7,045,553 B2 | 5/2006 | Hershkowitz | |
| 7,053,128 B2 | 5/2006 | Hershkowitz | |
| 7,119,240 B2 | 10/2006 | Hall et al. | |
| 7,208,647 B2 | 4/2007 | Peterson et al. | |
| 7,217,303 B2 | 5/2007 | Hershkowitz et al. | |
| 7,288,127 B1 | 10/2007 | Wulff et al. | |
| 7,491,250 B2 | 2/2009 | Hershkowitz et al. | |
| 7,503,948 B2 | 3/2009 | Hershkowitz et al. | |
| 7,815,873 B2 | 10/2010 | Sankaranarayanan et al. | |
| 7,815,892 B2 | 10/2010 | Hershkowitz et al. | |
| 7,846,401 B2 | 12/2010 | Hershkowitz et al. | |
| 2002/0020113 A1 | 2/2002 | Kennedy et al. | |
| 2003/0235529 A1 | 12/2003 | Hershkowitz et al. | |
| 2004/0170559 A1 | 9/2004 | Hershkowitz et al. | |
| 2004/0191166 A1 | 9/2004 | Hershkowitz et al. | |
| 2005/0154068 A1* | 7/2005 | Hershkowitz et al. | 518/703 |
| 2005/0201929 A1 | 9/2005 | Hershkowitz et al. | |
| 2007/0144940 A1 | 6/2007 | Hershkowitz et al. | |
| 2008/0142409 A1 | 6/2008 | Sankaranarayanan et al. | |

FOREIGN PATENT DOCUMENTS

| | | |
|---|---|---|
| FR | 841 410 | 5/1939 |
| GB | 763 675 | 12/1956 |
| GB | 830 574 | 3/1960 |
| GB | 855 764 | 12/1960 |
| GB | 959 818 | 6/1964 |
| GB | 972 153 | 10/1964 |
| GB | 1 064 447 | 4/1967 |
| GB | 1 149 798 | 4/1969 |
| GB | 1 216 496 | 12/1970 |
| GB | 2 265 380 | 9/1993 |
| GB | 2 265 381 | 9/1993 |
| GB | 2 265 382 | 9/1993 |

OTHER PUBLICATIONS

Bartholome, Methods of Energy Addition for Endothermic Gas Reactions at High Temperatures, Zeitschrift fuer Elektrochemie und Angewandte Physikalische Chemie (1953), 57, pp. 497-502. (with Machine Translation).

Bixler and Coberly, Wulff—Process Acetylene, Journal of Industrial and Engineering Chemistry (Washington, D.C.) (1953), 45, pp. 2596-2606.

Bogart and Dodd, Recent Developments in Wulff Acetylene, Chemical Engineering Progress (1954), 50, pp. 372-375.

Bogart, Schiller, and Coberly, The Wulff Process for Acelylene from Hydrocarbons, Petroleum Processing (1953), 8, pp. 377-382.

Gueret, Christopher et al., "*Methane Pyrolysis: Thermodynamics*", Chemical Engineering Science, 1997, vol. 52, No. 5, pp. 815-827.

Holmen, Anders et al., "Pyrolysis of natural gas: chemistry and process concepts", Elsevier Science B.V., Fuel Processing Technology 42 (1995), pp. 249-267.

Jennings, Organic Chemicals from Natural Gas, Chemical & Process Engineering (1952), 33, pp. 243-246.

Kolios, J. et al., *Autothermal Fixed-Bed Reactor Concepts*, Chemical Engineering Science, 2000, vol. 55, pp. 5945-5967.

Matros, Y. et al., *Reverse-Flow Operation in Fixed Bed Catalytic Reactors*, Catalysis Reviews: Science and Engineering, 1996, vol. 38(1), pp. 1-68.

Ries, H. C., Acetylene, Process Economics Program, Stanford Research Institute, Report No. 16, Menlo Park, CA, Sep. 1966, pp. 1-403.

China and the Japanese Petrochemical Industry, Chemical Economy and Engineering Review, Jul./Aug. 1985, vol. 17, No. 7-8 (No. 190), pp. 47-48.

Sherwood, Peter W., Acetylene from Natural Gas and Petroleum, Erdoel und Kohle (1954), 7, pp. 819-822, (with Machine Translation).

Sneddon, "Successful Acetylene Synthesis", The Petroleum Engineer—Synthesis of Petrochemicals—6 (Jan. 1954), 26, pp. C5-C8.

Weaver, Processing Engineering—Economics of Acelylene by Wulff Process, Chemical Engineering Progress (1953), 49, pp. 35-39.

* cited by examiner

Reforming Step

Regeneration Step

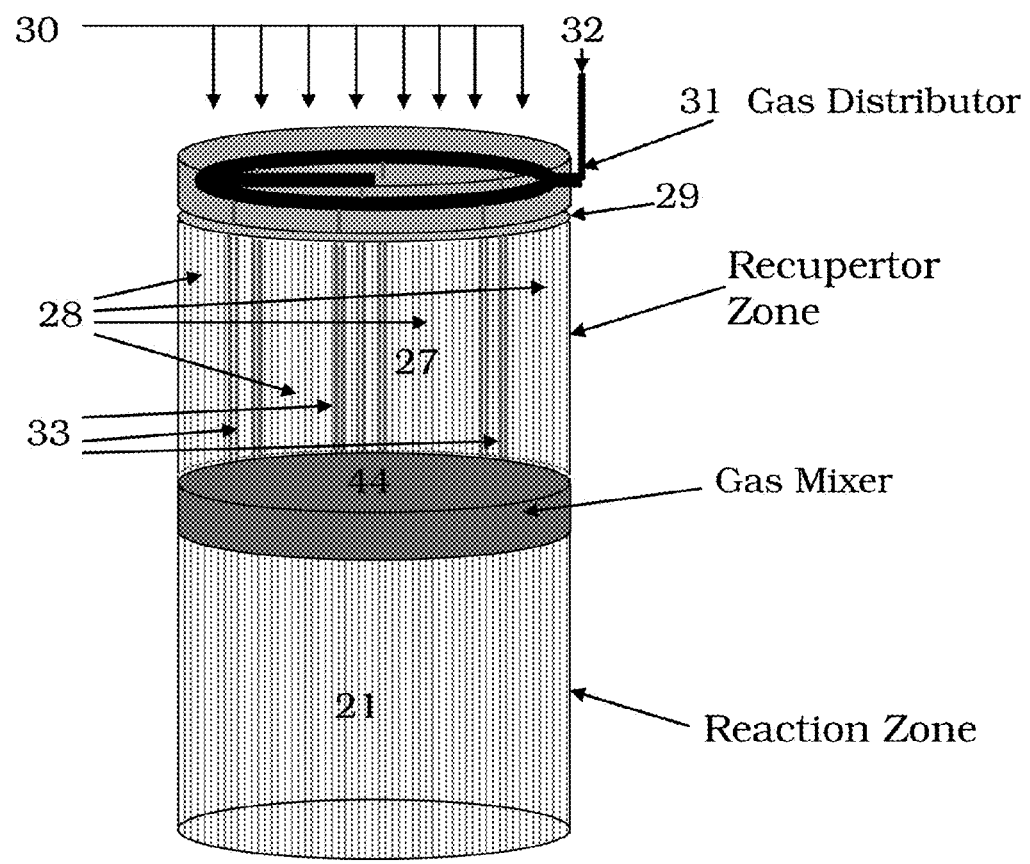

METHANE CONVERSION TO HIGHER HYDROCARBONS

CROSS REFERENCE TO RELATED APPLICATIONS

This application is a divisional of U.S. application Ser. No. 11/643,541, filed Dec. 21, 2006 now U.S. Pat. No. 7,943,808, which claims benefit of and priority to U.S. Provisional Application No. 60/753,961, filed Dec. 23, 2005, the entirety of which is incorporated herein by reference. This application is also a continuation in part of U.S. Ser. No. 11/639,691, filed Dec. 15, 2006 now U.S. Pat. No. 7,846,401 which is not incorporated by reference herein.

FIELD OF THE INVENTION

The invention relates to the manufacture of acetylene from methane. The present invention also relates broadly to regenerative reactors. More particularly the invention relates to an improved process and apparatus for producing acetylene from a methane feed by controlling combustion for thermal regeneration of reverse flow regenerative reactors in a unique and thermally efficient way.

BACKGROUND OF THE INVENTION

Acetylene (or ethyne, HC≡CH) has long been recognized as one of the few compounds that can be made directly at high selectivity from methane but the conditions of that manufacture have placed it beyond commercial practicality for other than high cost, specialty production. Acetylene can be converted to a number of other desirable hydrocarbon products, such as olefins and vinyls. One of the biggest impediments to producing acetylene from methane feeds has been the very high temperatures required to produce high-yield conversion of methane to acetylene. Many of the desired products that could be manufactured from the produced acetylene are today instead being produced via more economical processes, such as thermal cracking of higher molecular weight hydrocarbon feeds such as ethane and naphthas, in thermal crackers. The higher molecular weight feed crack at lower temperatures than methane. Equipment, materials, and processes were not previously identified that could continuously withstand the high (>1600° C.) temperatures required for methane pyrolysis. Pyrolyzing large quantities of methane had been considered much too costly and impractical due to the special types and costs of equipment that would be required. The developed processes for producing acetylene have all operated commercially at lower temperatures for steam cracking of higher weight hydrocarbon feeds.

It is known that acetylene may be manufactured from methane in small amounts or batches, using a high temperature, short contact time, yielding a mixture of acetylene, CO, and $H_2$. Comprehensive discussions are provided in the Stanford Research Institute report entitled "Acetylene," a Process Economics Program, Report No. 16, September 1966, and in the Fuel Processing Technology publication (42), entitled "Pyrolysis of Natural Gas: Chemistry and Process Concepts," by Holmen, et. al., 1995, pgs. 249-267. However, the known processes are inefficient, do not scale well, and are generally only useful for specialty applications.

The known art discloses that to efficiently obtain relatively high yields of acetylene, such as in excess of 50 wt % or more preferably in excess of 75 wt % acetylene from the methane feed, temperatures are required to be in excess of 1500° C. and preferably in excess of 1600° C., and with short contact times (generally <0.1 seconds) to prevent breaking the acetylene into elemental carbon and hydrogen components. Such temperature and processes have largely been unattractive due to the degradation of the equipment utilized. Virtually any metal components that are exposed to such temperatures will be costly and will unacceptably degrade.

In addition to the above references, U.S. Pat. No. 2,813,919 discloses acetylene manufacture from methane in a reverse-flow reactor (a regenerative furnace), operating at temperatures of typically 2500° F. (1370° C.), but up to 3000° F. (1650° C.). U.S. Pat. No. 2,885,455 discloses a reverse-flow reactor (a regenerative pebble-bed reactor) for production of acetylene from light hydrocarbons. Ethane and propane feeds are discussed and claimed; methane is not mentioned. Reaction temperatures up to 3000° F. (1650° C.) and contact times of 0.1 second or less are disclosed. U.S. Pat. No. 2,886,615 describes a reverse-flow reactor (a regenerative pebble-bed reactor) useful for processing hydrocarbon feed stocks (including natural gas) with hydrogen reactant to prepare olefins, acetylenes, and other product. Temperatures in excess of 3000° F. (1650° C.) and reaction times of 0.001 to 1 second are disclosed. The improvement taught is a secondary heat reservoir.

U.S. Pat. No. 2,920,123 describes pyrolysis of methane to produce acetylene at temperatures of 2820° F. (1550° C.) to 2910° F. (1600° C.) and contact time in the range of 0.004 to 0.015 seconds. The exemplified reactor is an electrically heated ceramic tube, and the soft carbon produced as a byproduct under these conditions is removed by oxidation after 5 seconds of feed.

U.S. Pat. No. 3,093,697 discloses a process for making acetylene by heating a mixture of hydrogen and a hydrocarbon stock (e.g., methane) at a reaction temperature that is dependent upon the particular hydrocarbon employed, for about 0.01 to 0.05 second. The reference indicates that a reaction temperature of 2700° F. to 2800° F. (about 1482° C. to about 1538° C.) is preferred for methane and that lower temperatures are preferred for higher molecular weight hydrocarbons.

U.S. Pat. No. 3,156,733 discloses a process for the pyrolysis of methane to acetylene and hydrogen. The process involves heating a methane-containing stream in a pyrolytic reaction zone at a maximum temperature above 2730° F. (1500° C.) and sequentially withdrawing a gaseous product from the reaction zone and quenching the product rapidly to a temperature of about 1100° F. (600° C.) or less. U.S. Pat. No. 4,176,045 discloses a process for the production of olefins by steam-cracking normally liquid hydrocarbons in a tubular reactor wherein the residence time in the tubes is from about 0.02 to about 0.2 second and the formation of coke deposits in the tubular reactor is minimized. U.S. Pat. No. 4,929,789 discloses a process for pyrolyzing or thermal cracking a gaseous or vaporized hydrocarbon feedstock using a novel gas-solids contacting device and an oxidation catalyst. U.S. Pat. No. 4,973,777 discloses a process for thermally converting methane into hydrocarbons with higher molecular weights using a circulating methane atmosphere in a ceramic reaction zone.

Chemical Economy and Engineering Review, July/August 1985, Vol. 17, No. 7.8 (No. 190), pp. 47-48, discloses that furnaces have been developed commercially for steam cracking a wide range of liquid hydrocarbon feedstocks using process reaction times in the range of 0.05 to 0.1 second. This publication indicates that the use of these furnaces permits substantial increases in the yield of olefins (i.e., ethylene, propylene, butadiene) while decreasing production of less-desirable co-products. GB 1064447 describes a process for production of acetylene from pyrolysis of methane and hydrogen (1:1 to 39:1 $H_2$:$CH_4$; clm. 9) in an electrically heated reactor, and quenching with a dry, oxygen-free gas stream. The maximum temperature is 1450 to 2000° C. (preferably 1450 to 1750° C.; clm. 2).

The "Wulff" process represents one of the more preferred commercial processes for generation of acetylene. The Wulff process includes a reverse-flow thermal pyrolysis process and began development in the 1920's. Various related processes operated commercially up to about the 1960s. These processes typically used feeds heavier than methane and thereby operated at temperatures of less than 1500° C. The most complete description of the Wulff process is provided in the Stanford Research Institute's "Acetylene", Process Economics Program Report Number 16 (1966). Among the relevant patents listed in this report are U.S. Pat. Nos. 2,319,679; 2,678,339; 2,692,819; and 3,093,697, discussed above. It is believed that all commercial acetylene plants operated on feeds of ethane, naphtha, and/or butane, but that none have successfully operated on methane feeds. Wulff discloses a cyclic, regenerative furnace, preferably including stacks of Hasche tiles (see U.S. Pat. No. 2,319,579) as the heat exchange medium. However, to contain the location of the reaction heat generated by the exothermic combustion process, one of either the fuel or oxygen is introduced laterally or separately into the central core of the reactor where it mixes with the other reaction component. The other reaction component is preferably introduced through the reactor tiles to cool the reactor quench section. Thereby, combustion may occur in a known location within the reactor. However, this also exposes the lateral injection nozzles or ports to the combustion product, including the extremely high temperature needed to crack methane feeds. Degradation in nozzle performance, shape, and/or size consequently made it extremely difficult to control flame shape, temperature, and efficiency. Although some of the Wulff art disclose use of various refractory materials, a commercially useful process for methane cracking was not achieved utilizing such materials. Also, a further drawback of the Wulff process is that the laterally or separately introduced portion of exothermic reactant is not utilized for quenching the recuperation reactor bed.

Regenerative reactors, including reactors such as disclosed by Wulff, are typically used to execute cyclic, batch-generation, high temperature chemistry. Typically, regenerative reactor cycles are either symmetric (same chemistry or reaction in both directions) or asymmetric (chemistry or reaction changes with step in cycle). Symmetric cycles are typically used for relatively mild exothermic chemistry, examples being regenerative thermal oxidation ("RTO") and autothermal reforming ("ATR"). Asymmetric cycles are typically used to execute endothermic chemistry, and the desired endothermic chemistry is paired with a different chemistry that is exothermic (typically combustion) to provide heat of reaction for the endothermic reaction. Examples of asymmetric cycles are Wulff cracking processes and pressure swing reforming processes.

As mentioned above, regenerative reactors are known that separately deliver a stream of fuel, oxidant, or a supplemental amount of one of these reactants, directly to a location somewhere in the heat generation region of the reactor. Although this may defer or control location of combustion, that process limits the cooling of the quench regions of the reactor, due to not having that stream pass through regenerative beds or regions. This can result in expanding heat zones loss of reaction control.

The reactor heat generation region is typically a region of the reactor system that is in between two regenerative reactor beds or regions, with the main regenerative flow passing from one of these bodies to the other. In most cases, this lateral stream is introduced via nozzles, distributors, or burners (e.g., Wulff) that penetrate the reactor system using a means that is generally perpendicular to flow direction and usually through the reactor vessel side wall. In large scale operations, such methods are impermissibly inefficient and costly. For example, during the exothermic step in a conventional Wulff cracking furnace, air flows axially through the regenerative bodies, and fuel is introduced via nozzles that penetrate the side of the furnace, to combine with air (combusting and releasing heat) in an open zone between regenerative bodies. In a conventional symmetric RTO application, a burner is placed to provide supplemental combustion heat in a location in between two regenerative bodies. The burner combusts fuel from outside the reactor, either with the air passing through the regenerative bodies, or using external air. Additional measure must be made to ensure adequate and timely quenching of the synthesized product, and to adequately cool the bed before the next cycle begins.

Attempts have been made to introduce a reactant of the exothermic step to a location in the middle of the regenerative reactor via conduits that are positioned axially within one or more of the regenerative bodies. For example, Sederquist (U.S. Pat. No. 4,240,805) uses pipes that are positioned axially within the regenerative bed to carry oxidant (air) to locations near the middle of the regenerative flow path.

All of these previously known systems suffer disadvantages that render the same inefficient and unpractical in any but very specialized, small scale operations with methane feeds. Positioning nozzles, distributors, or burners in the middle of the regenerative flow path of the reactor diminishes the durability and control of the reactor system. Nozzles, distributors, and/or burners all rely on carefully-dimensioned passages to regulate flow in a uniform manner, or to create the turbulence or mixing required to evenly distribute the heat that results from the exothermic reaction they support. These nozzles, distributors, and/or burners are located at the highest-temperature part of the reactor. It is very difficult to fabricate and maintain carefully-dimensioned shapes for use at high temperatures. If the nozzles or distributor loses its carefully-dimensioned shape, it will no longer produce uniform flame temperatures.

A further disadvantage of separately or laterally introducing one or more reactant directly into the middle or heat region of the regenerative flow path of the reactor is that such an arrangement bypasses that reactant around the regenerative flow path. In addition to not quenching the quench portion of the reactor, such approach also eliminates preheating that reactant stream. The fundamental purpose of a regenerative reactor system is ideally to execute reactions at high efficiency by recuperating product heat directly into feeds. Bypassing some fraction of the feed to the reactor around the regenerative system thus reduces the efficiency potential of the reactor system and can lead to expanded heat zones and feed conversion reactions that last too long.

All of the known art disclose processes, methods, and equipment that are unsuitable for continuous, high efficiency operation at the necessarily high temperature, due to complexity and thermal degradation of equipment. Also, the known processes do not reliably provide methods or means for continuously controlling the location and dissipation of the created heat, resulting in either hot spots, undesired thermal migration, and/or inefficient processes. What is needed is an efficient and cost-effective way to pyrolyze methane to acetylene at relatively high yield, selectivity, and efficiency, in a manner that is competitive with pyrolyzing other hydrocarbon feeds to acetylene.

SUMMARY OF THE INVENTION

The present inventors have discovered that acetylene can be efficiently manufactured from methane feed according to the inventive reverse-flow regenerative reactor system, method, and process. This invention provides processes and apparatus for efficiently converting methane by controlling location, movement, and removal of reaction heat. The inventive process beneficially feeds all of the exothermically reacting regeneration reactant streams through the recuperation or quenching reactor bed media, while simultaneously deferring combustion, until the reactants reach a desired region of the reactor system. The invention also includes use of an inventive mixing apparatus within the high heat region to provide efficient and complete mixing and exothermic reaction within the reactor system. The inventive process also preferably utilizes hydrogen as a methane synthesis reaction diluent. The inventive process creates and confines a regenerating "heat bubble" within the reactor system, without exposing any degradable components to the high heat. The inventive process consistently provides controlled exothermic reaction location and temperature migration and successfully avoids equipment heat degradation.

In one preferred aspect, the invention includes a process for the manufacture of acetylene from methane feed using a cyclic reverse-flow reactor system, wherein the reactor system includes (i) a first reactor comprising a first end and a second end, and (ii) a second reactor comprising primary end and a secondary end, the first and second reactors oriented in a series relationship with respect to each other such that the secondary end of the second reactor is proximate the second end of the first reactor, the process comprising the steps of:
  (a) supplying a first reactant through a first channel in the first reactor and supplying at least a second reactant through a second channel in the first reactor, such that the first and second reactants are supplied to the first reactor from the first end of the first reactor;
  (b) combining the first and second reactants at the second end of the first reactor and reacting the combined reactants to exothermically produce a heated reaction product;
  (c) passing the heated reaction product through the second reactor to transfer heat from the reaction product to the second reactor;
  (d) thereafter supplying methane through the heated second reactor to the first reactor, to convert at least a portion of the methane into acetylene;
  (e) passing the supplied methane and the produced acetylene through the first reactor to quench the methane and the produced acetylene; and
  (f) recovering the produced acetylene.

In another aspect, the invention includes a cyclic reverse flow reactor system for the manufacture of acetylene from methane feed, wherein the reactor system comprises:
  (i) a first reactor comprising a first end and a second end;
  (ii) a second reactor comprising primary end and a secondary end, the first and second reactors oriented in a series relationship with respect to each other such that the secondary end of the second reactor is proximate the second end of the first reactor;
    wherein the first reactor further comprises;
    (a) a first channel to supply at least a first reactant from the first end of the first reactor to the second end of the first reactor;
    (b) a second channel to supply at least a second reactant from the first end of the first reactor to the second end of the first reactor; and
    (c) a product removal line to remove at least one of methane and a produced acetylene from the first reactor;
    wherein the second reactor further comprises;
    (i) a flue gas removal line to remove at least a portion of the heated reaction product produced from mixing and reaction of the first and second reaction products; and
    (ii) a methane feed line to feed methane to the primary end of the second reactor. The second reactor may be configured with a bedding arrangement similar to the first bed, or the second bed may be configured in separate fashion, such as according to a known pyrolysis bed design.

The first channel and the second channel in the first reactor maintains separated flow paths for the first and second reactants to prevent at least a majority (by stoichiometric reactivity) of the first reactant and the second reactant from exothermically reacting with each other within the first reactor. This defers reaction of the majority of reactant until the same exits the second end of the first reactor.

BRIEF DESCRIPTION OF THE DRAWINGS

FIG. 2 is another diagrammatic illustration of an exemplary regenerative bed reactor that defers combustion, controls the location of the exothermic reaction, and adequately quenches the recuperation reactor bed.

DETAILED DESCRIPTION

Figure 1A:
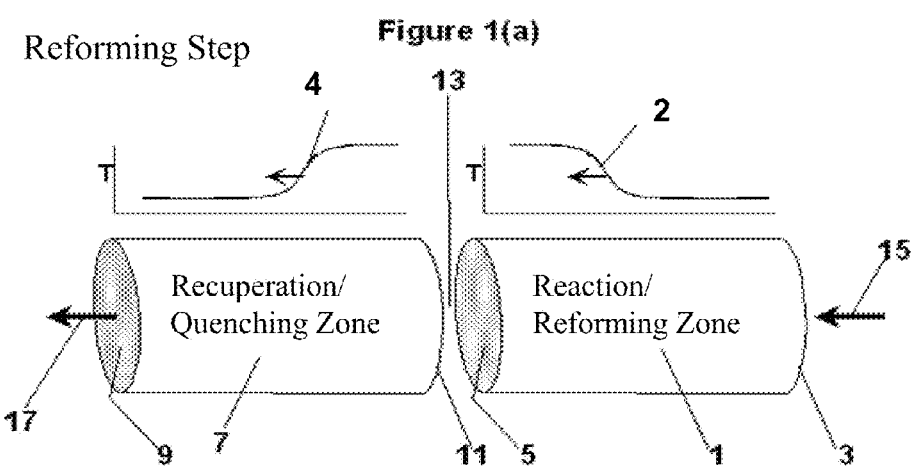
FIGS. 1(a) and 1(b) are a diagrammatic illustration of the two steps in a regenerating reverse flow reactor according to the present invention.

According to the invention, methane is converted to acetylene in a reverse-flow reactor by pyrolysis, preferably at temperatures of from about 1500 to about 1900° C., and more preferably from about 1600 to about 1700° C., with short residency times, e.g., less than 0.1 seconds and preferably less than about 5 milliseconds, and preferably in the presence of hydrogen diluent. The conversion of methane into higher hydrocarbons such as acetylene requires a high reformation temperature, which in the past has been a barrier to commercialization and efficiency.

At least part of the invention of the present inventors is the recognition that the requisite high heat may be achieved by creating a high-temperature heat bubble in the middle of a packed bed system and then use a two-step process wherein heat is (1) added to the bed via in-situ combustion, and then (2) removed from the bed via in-situ endothermic reforming. A key benefit of the invention is the ability to consistently manage and confine the high temperature bubble (e.g., >1600° C.) in a reactor region(s) that can tolerate such conditions long term. The inventive process provides for a substantially continuously operating, large-scale, cyclic, reverse-flow reactor system that is useful and operable on a commercial scale. This invention overcomes the limitations of the prior art.

One common source for methane is natural gas. In some applications, natural gas, including associated hydrocarbon and impurity gases, may be supplied into the inventive reactor system. The supplied natural gas also may be sweetened and/or dehydrated natural gas. Natural gas commonly includes various concentrations of associated gases, such as ethane and other alkanes, preferably in lesser concentrations than methane. The supplied natural gas may include impurities, such as H2S and nitrogen. The inventive methods and apparatus may also serve to simultaneously convert some fraction of the associated higher hydrocarbons to acetylene. In other embodiments, the inventive methods and compositions may be utilized with liquid feeds, such a vacuum gas oil (VGO) or naphthas.

The present invention may be described as methane pyrolysis in a reverse flow reactor system or more specifically the conversion of methane to acetylene via pyrolysis of methane in a reverse-flow reactor system. The reactor system includes first and second reactors, oriented in a series relationship with each other with respect to a common flow path, and preferably along a common axis. The common axis may be horizontal, vertical, or otherwise. The present invention includes a process wherein: first and second in-situ combustion reactants are both separately, but preferably substantially simultaneously, passed through a quenching reactor bed (e.g., a first reactor bed), via substantially independent flow paths (channels), to obtain the quenching (cooling) benefits of the total combined weight of the first and second reactants. (Although only first and second reactants are discussed, the regeneration reaction may also include additional reactants and reactant flow channels.) Both reactants are also concurrently heated by the hot quench bed, before they reach a designated location within the reactor system and react with each other in an exothermic reaction zone (e.g., a combustion zone). This deferred combustion of the first and second reactants permits positioning initiation of the exothermic regeneration reaction at the desired location within the reactor system.

The reactants are permitted to combine or mix in the reaction zone to combust therein, in-situ, and create a high temperature zone or heat bubble (1600-1700° C.) inside of the reactor system. Preferably the combining is enhanced by a reactant mixer that mixes the reactants to facilitate substantially complete combustion/reaction at the desired location, with the mixer preferably located between the first and second reactors. The combustion process takes place over a long enough duration that the flow of first and second reactants through the first reactor also serves to displace a substantial portion, (as desired) of the heat produced by the reaction (e.g., the heat bubble), into and at least partially through the second reactor, but preferably not all of the way through the second reactor to avoid waste of heat and overheating the second reactor. The flue gas may be exhausted through the second reactor, but preferably most of the heat is retained within the second reactor. The amount of heat displaced into the second reactor during the regeneration step is also limited or determined by the desired exposure time or space velocity that the methane feed gas will have to the reforming, high temperature second reactor media to convert the methane and other hydrocarbons to acetylene.

After regeneration or heating the second reactor media, in the next/reverse step or cycle, methane is supplied or flowed through the second reactor, from the direction opposite the direction of flow during the heating step. The methane contacts the hot second reactor and mixer media, in the heat bubble region, to transfer the heat to the methane for reaction energy. In addition to not wasting heat, substantially overheating the reformer/second reactor bed may adversely lead to a prolonged reaction that cracks the methane past the acetylene generation point, breaking it down into its elemental components. Thus, the total amount of heat added to the bed during the regeneration step should not exceed the sum of the heats that are required (a) to sustain the reforming reaction for the endothermic conversion of the supplied methane to acetylene for a suitable period of time, as determined by many factors, such as reactor size, dimensions, gas flow rates, temperatures used, desired contact time, cycle duration, etc, and (b) for heat losses from the system both as conduction losses through reactor walls as well as convective losses with the exiting products. The total amount of heat stored in the reactor system though is generally much more heat than would be minimally needed for conversion on any single cycle. However, it is desirable to avoid having the temperature bubble so large that the residence time at temperature becomes too long. As is commonly done for reactor systems, normal experimentation and refining adjustments and measurements can be made to the reactor system to obtain the optimum set of reactor conditions.

In preferred embodiments, the reactor system may be described as comprising two zones/reactors: (1) a heat recuperating (first) zone/reactor, and (2) a reforming (second) zone/reactor. As a catalyst is not required to facilitate reforming methane to acetylene, in most preferred embodiments no catalyst is present in the reactor beds. However, there may be some applications that benefit from the presence of a catalyst to achieve a certain range of reforming performance and such embodiments are within the scope of the invention.

Figure 1B:
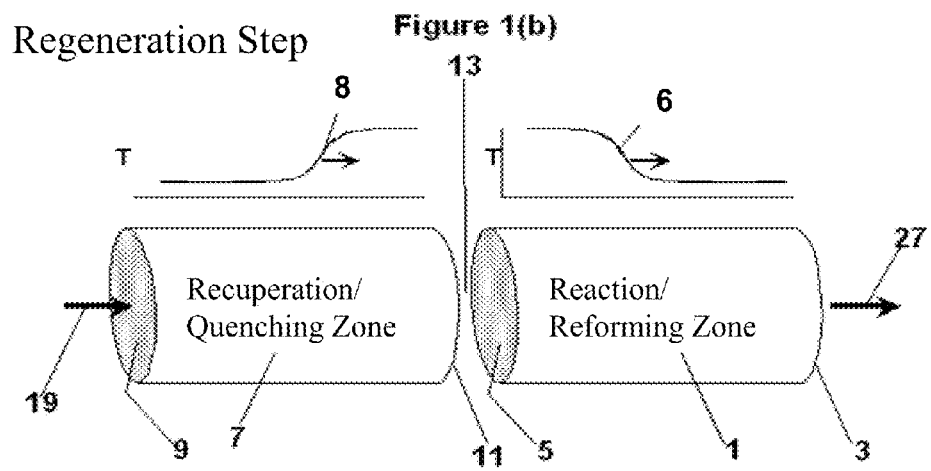

The basic two-step asymmetric cycle of a reverse flow regenerative bed reactor system is depicted in FIGS. 1a and 1b in terms of a reactor system having two zones/reactors; a first or recuperator/quenching zone (7) and a second or reaction/reforming zone (1). Both the reaction zone (1) and the recuperator zone (7) contain regenerative beds. Regenerative beds, as used herein, comprise materials that are effective in storing and transferring heat. The term regenerative reactor bed(s) means a regenerative bed that may also be used for carrying out a chemical reaction. The regenerative beds may comprise bedding or packing material such as glass or ceramic beads or spheres, metal beads or spheres, ceramic (including zirconia) or metal honeycomb materials, ceramic tubes, extruded monoliths, and the like, provided they are competent to maintain integrity, functionality, and withstand long term exposure to temperatures in excess of 1200° C., preferably in excess of 1500° C., more preferably in excess of 1700° C., and even more preferably in excess of 2000° C. for operating margin.

As shown in FIG. 1a, at the beginning of the "reaction" step of the cycle, a secondary end (5) of the reaction zone (1) (a.k.a. herein as the reformer or second reactor) is at an elevated temperature as compared to the primary end (3) of the reaction bed (1), and at least a portion (including the first end (9)) of the recuperator or quench zone (7), is at a lower temperature than the reaction zone (1) to provide a quenching effect for the synthesis gas reaction product. A methane containing reactant feed, and preferably also a hydrogen diluent, is introduced via a conduit(s) (15), into a primary end (3) of the reforming or reaction zone (1). Thereby, in a preferred embodiment, the term pyrolysis includes hydropyrolysis.

The feed stream from inlet(s) (15) absorbs heat from the reformer bed (1) and endothermically reacts to produce the desired acetylene product. As this step proceeds, a shift in the temperature profile (2), as indicated by the arrow, is created based on the heat transfer properties of the system. When the bed is designed with adequate heat transfer capability, this profile has a relatively sharp temperature gradient, which gradient will move across the reaction zone (1) as the step proceeds. The sharper the temperature gradient profile, the better the reaction may be controlled.

The methane/hydrogen/acetylene reaction gas exits the reaction zone (1) through a secondary end (5) at an elevated temperature and passes through the recuperator reactor (7), entering through a second end (11), and exiting at a first end (9) as a synthesized gas comprising acetylene, some unconverted methane, and hydrogen. The recuperator (7) is initially at a lower temperature than the reaction zone (1). As the synthesized reaction gas passes through the recuperator zone (7), the gas is quenched or cooled to a temperature approaching the temperature of the recuperator zone substantially at the first end (9), which in some embodiments is preferably approximately the same temperature as the regeneration feed introduced via conduit (19) into the recuperator (7) during the second step of the cycle. As the reaction gas is cooled in the recuperator zone (7), a temperature gradient (4) is created in the zone's regenerative bed(s) and moves across the recuperator zone (7) during this step. The quenching heats the recuperator (7), which must be cooled again in the second step to later provide another quenching service and to prevent the size and location of the heat bubble from growing progressively through the quench reactor (7). After quenching, the reaction gas exits the recuperator at (9) via conduit (17) and is processed for separation and recovery of the various components.

The second step of the cycle, referred to as the regeneration step, then begins with reintroduction of the first and second regeneration reactants via conduit(s) (19). The first and second reactants pass separately through hot recuperator (7) toward the second end (11) of the recuperator (7), where they are combined for exothermic reaction or combustion in or near a central region (13) of the reactor system.

The regeneration step is illustrated in FIG. 1*b*. Regeneration entails transferring recovered sensible heat from the recuperator zone (7) to the reaction zone (1) to thermally regenerate the reaction beds (1) for the subsequent reaction cycle. Regeneration gas/reactants enters recuperator zone (7) such as via conduit(s) (19), and flows through the recuperator zone (7) and into the reaction zone (1). In doing so, the temperature gradients (6) and (8) may move across the beds as illustrated by the arrows on the exemplary graphs in FIG. 1(*b*), similar to but in opposite directions to the graphs of the temperature gradients developed during the reaction cycle in FIG. 1(*a*). Fuel and oxidant reactants may combust at a region proximate to the interface (13) of the recuperator zone (7) and the reaction zone (1). The heat recovered from the recuperator zone together with the heat of combustion is transferred to the reaction zone, thermally regenerating the regenerative reaction beds (1) disposed therein.

In a preferred embodiment of the present invention, a first reactant, such as fuel, is directed down certain channels (each channel preferably comprising a reactant flow path that includes multiple conduits) in the first reactor bed (7). In one embodiment, the channels include one or more honeycomb monolith type structures. Honeycomb monoliths include extruded porous structures as are generally known in the reaction industry, such as in catalytic converters, etc. The term "honeycomb" is used broadly to refer to a cross-sectional shape that includes multiple flow paths or conduits through the extruded monolith and is not intended to limit the structure or shape to any particular shape. The honeycomb monolith enables low pressure loss transference while providing contact time and heat transfer. A mixer is preferably used between the zones to enable combustion. Each channel of the first and second channels is defined broadly to mean the conductive conduit(s) or flow path(s) by which one of the reactants and synthesis gas flows through the first reactor bed (7) and may include a single conduit or more preferably and more likely, multiple conduits (e.g., tens, hundreds, or even thousands of substantially parallel conduit tubes) that receive feed, such as from a gas distributor nozzle or dedicated reactant port.

The conduits each may have generally any cross-sectional shape, although a generally circular or regular polygon cross-sectional shape may be preferred. Each channel may preferably provide substantially parallel, generally common flow through the reactor media. Thus, a first channel may be merely a single conduit, but more likely will be many conduits, (depending upon reactor size, flow rate, conduit size, etc.), for example, such as exemplified in FIG. 2 and in Example 1 below. A channel preferably includes multiple conduits that each receive and conduct a reactant, such as delivered by a nozzle in a gas distributor. The conduits may be isolated from each other in terms of cross flow along the flow path (e.g. not in fluid communication), or they may be substantially isolated, such that reactant permeation through a conduit wall into the adjacent conduit is substantially inconsequential with respect to reactant flow separation. One preferred reactor embodiment includes multiple segments, whereby each segment includes a first channel and a second channel, such that after exiting the reactor, the respective first reactant is mixed with the respective second reactant in a related mixer segment. Multiple segments are included to provide good heat distribution across the full cross-sectional area of the reactor system.

Figures 4, 4A:
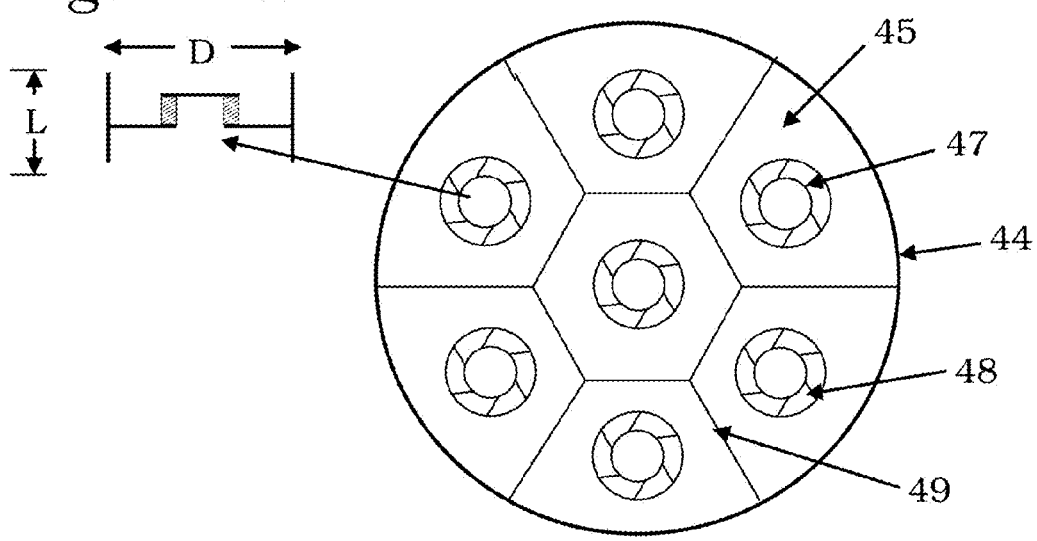
FIG. 4 illustrates a cross sectional view of an exemplary gas mixer and channels for controlled combustion.
FIG. 4a is a cutout view of a portion of FIG. 4.

Referring to FIG. 4, mixer segment (45), for example, may mix the reactant flows from multiple honeycomb monoliths arranged within a particular segment. Each monolith preferably comprises a plurality (more than one) of conduits. The collective group of conduits that transmit the first reactant may be considered the first channel and a particular reactor segment may include multiple collective groups of monoliths and/or conduits conducting the first reactant, whereby the segment comprising a channel for the first reactant. Likewise, the second reactant may also flow through one or more monoliths within a segment, collectively constituting a second channel. Thus, the term "channel" is used broadly to include the conduit(s) or collective group of conduits that conveys at least a first or second reactant. A reactor segment may include only a first and second channel, or multiple channels for multiple flow paths for each of the first and second reactants. A mixer segment (45) may then collect the reactant gas from both or multiple channels. Preferably, a mixer segment (45) will mix the effluent from one first channel and one second channel.

It is recognized that in some preferred embodiments, several of the conduits within a channel will likely convey a mixture of first and second reactants, due at least in part to some mixing at the first end (17) of the first reactor. However, the numbers of conduits conveying combustible mixtures of first and second reactants is sufficiently low such that the majority of the stoichiometrically reactable reactants will not react until after exiting the second end of the first reactor. The axial location of initiation of combustion or exothermic reaction within those conduits conveying a mixture of reactants is controlled by a combination of temperature, time, and fluid dynamics. Fuel and oxygen usually require a temperature-dependent and mixture-dependent autoignition time to combust. Still though, some reaction will likely occur within an axial portion of the conduits conveying a mixture of reactants. However, this reaction is acceptable because the number of channels having such reaction is sufficiently small that there is only an acceptable or inconsequential level of effect upon the overall heat balance within the reactor. The design details of a particular reactor system should be designed so as to avoid mixing of reactants within the conduits as much as reasonably possible.

The process according to the present invention requires no large pressure swings to cycle the reactants and products through the reactor system. In some preferred embodiments, the reforming or pyrolysis of methane step occurs at relatively low pressure, such as less than about 50 psia, while the regeneration step may also be performed at similar pressures, e.g., less than about 50 psia, or at slightly higher, but still relatively low pressures, such as less than about 250 psia. In some preferred embodiments, the methane pyrolysis step is performed at a pressure of from about 5 psia to about 45 psia, preferably from about 15 psia to about 35 psia. Ranges from about 5 psia to about 35 psia and from about 15 psia to about 45 psia are also contemplated. The most economical range may be determined without more than routine experimentation by one of ordinary skill in the art in possession of the present disclosure. Pressures higher or lower than that disclosed above may be used, although they may be less efficient. By way of example, if combustion air is obtained from extraction from a gas turbine, it may be preferable for regeneration to be carried out at a pressure of, for example, from about 100 psia to about 250 psia. However if, by way of further example, the process is more economical with air obtained via fans or blowers, the regeneration may be carried out at 15-45 psia. In one embodiment of the present invention, the pressure of the pyrolysis and regeneration steps are essentially the same, the difference between the pressures of the two steps being less than about 10 psia.

It is understood that some method of flow control (e.g. valves, rotating reactor beds, check valves, louvers, flow restrictors, timing systems, etc.) is used to control gas flow, actuation, timing, and to alternate physical beds between the two flow systems. In the regeneration step, air and fuel must be moved through the reactor system and combined for combustion. Air can be moved such as via compressor, blower, or fan, depending on the operating conditions and position desired for the reactor. If higher pressure air is used, it may be desirable to expand the flue gas through an expansion turbine to recover mechanical energy. In addition, some fraction of exhaust gas may be recycled and mixed with the incoming air. An exhaust gas recycle (EGR) stream may be supplied with at least one of the supplied first reactant and second reactant in the first reactor. This EGR may be used to reduce the oxygen content of the regeneration feed, which can reduce the maximum adiabatic flame temperature of the regeneration feed. In the absence of EGR, CH4/air mixtures have a maximum adiabatic flame temperature of about 1980° C.; H2/air mixtures are about 2175° C. Thus, even if average temperature is controlled by limiting the flow rate of fuel, any poor diluting could result in local hot spots that approach the maximum flame temperature. Use of EGR can reduce the maximum hot spot temperature by effectively increasing the amount of diluent such as N2 (and combustion products) that accompany the oxygen molecules.

For example, when 50% excess air is used for combustion, the maximum adiabatic flame temperature for H2-fuel/air combustion decreases from about 2175° C. to about 1640° C. Reducing the oxygen content of the supplied air to about 13% would make about 1640° C. the maximum adiabatic flame temperature, regardless of local mixing effects. The reforming or pyrolysis step and flow scheme is illustrated in FIG. 1(a). Methane (such as from natural gas) is supplied, preferably mixed with or supplied with hydrogen as a diluent, either within the second reactor or immediately prior to entry into the second reactor, and is pyrolyzed in the high temperature heat bubble created by the regeneration step. The methane containing feed may also include substantially any other hydrocarbon material that undergoes the endothermic reforming to acetylene, including natural gas, other petroleum alkanes, petroleum distillates, kerosene, jet fuel, fuel oil, heating oil, diesel fuel and gas oil, gasoline, and alcohols. Preferably, the feed will be gaseous material comprising methane and/or hydrocarbons that are in a gaseous state at the temperature and pressure of introduction into the reactor.

After leaving the second reactor and the optional mixer, the acetylene containing synthesized gas stream must be cooled or quenched to halt the conversion process at the acetylene stage. The timing for this step is important because acetylene is rarely a desired material for process export. Rather, a preferred use for the produced acetylene is as an intermediate product in a flow process within a chemical plant, in route to other preferred products, such as vinyl esters, ethylene, acetaldehyde, propanal, and/or or propanol, acrylic acid, and so on. After quenching, the synthesized gas stream may be provided to a separation process that separates the acetylene, methane, hydrogen, and other gases. Recovered methane and hydrogen may be recycled for processing again in the reactor system. A separate process sequence may convert the acetylene to some other product. Each of these products may be further processed to provide yet additional useful products, e.g., acetaldehyde is typically an intermediate in the manufacture of ethanol, acetic acid, butanals, and/or butanols.

Ethylene is a basic building block of a plethora of plastics, and may typically be the preferred use for the created acetylene, from the perspective of volume and value. Ethylene is conveniently manufactured from acetylene by hydrogenation. In some embodiments of the invention, it may also be a coproduct of the inventive methane conversion process.

Another product of high interest is ethanol, which may be conveniently manufactured by first hydrating the acetylene to acetaldehyde and then hydrogenating acetaldehyde to ethanol. Ethanol is of interest because it is easily transported from a remote location and is easily dehydrated to ethylene. Ethanol may also be suitable for use as a motor fuel, if the manufacturing can be sufficiently low in cost.

In any event, conversion of methane to acetylene leaves a surplus of hydrogen. The idealized reaction to acetylene is:

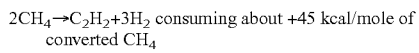

$2CH_4 \rightarrow C_2H_2 + 3H_2$ consuming about +45 kcal/mole of converted $CH_4$ As suggested by the above reaction, hydrogen is a valuable by-product of the present process. To a lesser extent, ethylene is also a valuable product, produced as a result of incomplete reduction of methane to higher hydrocarbon. Unreacted methane is also a valuable product.

Accordingly, separation and recovery of hydrogen, separation and recovery of ethylene, and separation and recovery of unconverted methane are each individually and collectively preferred steps in the process according to the invention. Unconverted methane is preferably returned to the hydropyrolysis reactor so that it may be converted on a second pass. An amount of hydrogen should also be returned to the hydropyrolysis reactor that is sufficient to control the selectivity of the product distribution.

Since hydrogen is created (not consumed) in the reforming pyrolysis reaction, it will be necessary to purge hydrogen from the process in the amount of about one H2 for every CH4 converted. Hydrogen has a heat of combustion of about 57 Kcal/mole H2, so the hydrogen purged from the process has a heating value that is in the range of what is needed as regeneration fuel. Of course, if there is an alternate, high-value use for the leftover hydrogen, then natural gas could be used for all or part of the regeneration fuel. But the leftover hydrogen is likely to be available at low pressure and may possibly contain methane or other diluents. So, use of hydrogen as regeneration fuel may also be an ideal disposition in a remote location.

FIG. 2 illustrates another exemplary reactor system that may be suitable in some applications for controlling and deferring the combustion of fuel and oxidant to achieve efficient regeneration heat. FIG. 2 depicts a single reactor system, operating in the regeneration cycle. The inventive reactor system may be considered as comprising two reactors zones. The recuperator (27) is the zone primarily where quenching takes place and provides substantially isolated flow paths or channels for transferring both of the quenching reaction gases through the reactor media, without incurring combustion until the gasses arrive proximate or within the reactor core (13) in FIG. 1. The reformer (2) is the reactor where regeneration heating and methane reformation primarily occurs, and may be considered as the second reactor for purposes herein. Although the first and second reactors in the reactor system are identified as separately distinguishable reactors, it is understood and within the scope of the present invention that the first and second reactors may be manufactured, provided, or otherwise combined into a common single reactor bed, whereby the reactor system might be described as comprising merely a single reactor that integrates both cycles within the reactor. The terms "first reactor" and "second reactor" merely refer to the respective zones within the reactor system whereby each of the regeneration, reformation, quenching, etc., steps take place and do not require that separate components be utilized for the two reactors. However, most preferred embodiments will comprise a reactor system whereby the recuperator reactor includes conduits and channels as described herein, and the reformer reactor may similarly possess conduits. Other preferred embodiments may include a reformer reactor bed that is arranged different from and may even include different materials from, the recuperator reactor bed. The bedding arrangement of the reformer or second reactor may be provided as desired or as prescribed by the application and no particular design is required herein of the reformer reactor, as to the performance of the inventive reactor system. Routine experimentation and knowledge of the methane pyrolysis art may be used to determine an effective reformer/second reactor design.

As discussed previously, the first reactor or recuperator (27) includes various gas conduits (28) for separately channeling two or more gases following entry into a first end (29) of the recuperator (27) and through the regenerative bed(s) disposed therein. A first gas (30) enters a first end of a plurality of flow conduits (28). In addition to providing a flow channel, the conduits (28) also comprise effective flow barriers (e.g., which effectively function such as conduit walls) to prevent cross flow or mixing between the first and second reactants and maintain a majority of the reactants effectively separated from each other until mixing is permitted. As discussed previously, each of the first and second channels preferably comprises multiple channels or flow paths. The first reactor may also comprise multiple substantially parallel flow segments, each comprising segregated first and second channels.

In a preferred embodiment of the present invention, the recuperator is comprised of one or more extruded honeycomb monoliths. Preferred honeycomb monoliths are extruded structures that comprise many (e.g., a plurality, meaning more than one) small gas flow passages or conduits, arranged in parallel fashion with thin walls in between. A small reactor may include a single monolith, while a larger reactor can include a number of monoliths, while still larger reactor may be substantially filled with an arrangement of many honeycomb monoliths. Each monolith may be formed by extruding monolith blocks with shaped (e.g., square or hexagonal) cross-section and two- or three-dimensionally stacking such blocks above, behind, and beside each other. Monoliths are attractive as reactor contents because they provide high heat transfer capacity with minimum pressure drop.

Each monolith may provide flow channel(s) (e.g., flow paths) for one of the first or second reactants. Each channel preferably includes a plurality of conduits. Alternatively, a monolith may comprise one or more channels for each reactant with one or more channels or groups of conduits dedicated to flowing one or more streams of a reactant, while the remaining portion of conduits flow one or more streams of the other reactant. It is recognized that at the interface between channels, a number of conduits will likely convey a mixture of first and second reactant, but this number of conduits is proportionately small. In other embodiments, a single flow channel may comprise multiple monoliths. Honeycomb monoliths preferred in the present invention (which are adjacent a first end (9) of the first reactor (7)) can be characterized as having open frontal area (or geometric void volume) between about 40% and 80%, and having conduit density between about 50 and 2000 pores per square inch, more preferably between about 100 and 1000 pores per square inch. (For example, in one embodiment, the conduits may have a diameter of only a few millimeters, and preferably on the order of about one millimeter.) Reactor media components, such as the monoliths or alternative bed media, preferably provide for at least one of the first and second channels and preferably both channels to include a packing with an average wetted surface area per unit volume that ranges from about 50 ft-1 to about 3000 ft-1, more preferably from about 100 ft-1 to 2500 ft-1, and still more preferably from about 200 ft-1 to 2000 ft-1, based upon the volume of the first reactor that is used to convey a reactant. These wetted area values apply to the channels for both of the first and second reactants. These relatively high surface area per unit volume values are likely preferred for many embodiments to aid achieving a relatively quick change in the temperature through the reactor, such as generally illustrated by the relatively steep slopes in the exemplary temperature gradient profile graphs, such as in FIGS. 1(a), 1(b), and 6. The quick temperature change is preferred to permit relatively quick and consistent quenching of the reaction to prevent the reaction from continuing and creating coke.

Preferred reactor media components also provide for at least one of the first and second channels in the first reactor and more preferably for both channels, to include a packing that includes a high volumetric heat transfer coefficient (e.g., greater than or equal to 0.02 cal/cm$^3$s° C., preferably greater than about 0.05 cal/cm$^3$s° C., and most preferably greater than 0.10 cal/cm$^3$s° C.), have low resistance to flow (low pressure drop), have operating temperature range consistent with the highest temperatures encountered during regeneration, have high resistance to thermal shock, and have high bulk heat capacity (e.g., at least about 0.10 cal/cm$^3$° C., and preferably greater than about 0.20 cal/cm$^3$° C.). As with the high surface area values, these relatively high volumetric heat transfer coefficient value and other properties are also likely preferred for many embodiments to aid in achieving a relatively quick change in the temperature through the reactor, such as generally illustrated by the relatively steep slopes in the exemplary temperature gradient profile graphs, such as in FIGS. 1(a), 1(b), and 6. The quick temperature change is preferred to permit relatively quick and consistent quenching of the reaction to prevent the reaction from continuing too long and creating coke or carbon buildup. The cited values are averages based upon the volume of reactor used for conveyance of a reactant.

Alternative embodiments may use reactor media other than the described and preferred honeycomb monoliths, such as whereby the channel conduits/flow paths may include a more tortuous pathways (e.g. convoluted, complex, winding and/or twisted but not linear or tubular), than the previously described monoliths, including but not limited to labyrinthine, variegated flow paths, conduits, tubes, slots, and/or a pore structure having channels through a portion(s) of the reactor and may include barrier portion, such as along an outer surface of a segment or within sub-segments, having substantially no effective permeability to gases, and/or other means suitable for preventing cross flow between the reactant gases and maintaining the first and second reactant gases substantially separated from each other while axially transiting the recuperator (27). For such embodiments, the complex flow path may create a lengthened effective flow path, increased surface area, and improved heat transfer. Such design may be preferred for reactor embodiments having a relatively short axial length through the reactor. Axially longer reactor lengths may experience increased pressure drops through the reactor. However for such embodiments, the porous and/or permeable media may include, for example, at least one of a packed bed, an arrangement of tiles, a permeable solid media, a substantially honeycomb-type structure, a fibrous arrangement, and a mesh-type lattice structure. It may be preferred that the media matrix provides high surface area to facilitate good heat exchange with the reactant and produced gases.

It may be preferred to utilize some type of equipment or method too direct a flow stream of one of the reactants into a selected portion of the conduits. In the exemplary embodiment of FIG. 2, a gas distributor (31) directs a second gas stream (32) to second gas stream channels that are substantially isolated from or not in fluid communication with the first gas channels, here illustrated as channels (33). The result is that at least a portion of gas stream (33) is kept separate from gas stream (30) during axial transit of the recuperator (27). In a preferred embodiment, the regenerative bed(s) of the recuperator zone comprise channels having a gas or fluid barrier that isolates the first reactant channels from the second reactant channels. Thereby, both of the at least two reactant gases that transit the channel means may fully transit the regenerative bed(s), to quench the regenerative bed, absorb heat into the reactant gases, before combining to react with each other in the combustion zone.

As used in the present invention, gases (including fluids) (30) and (32) each comprise a component that reacts with a component in the other reactant (30) and (32), to produce an exothermic reaction when combined. For example, each of the first and second reactant may comprise one of a fuel gas and an oxidant gas that combust or burn when combined with the other of the fuel and oxidant. By keeping the reactants substantially separated, the present invention defers or controls the location of the heat release that occurs due to exothermic reaction. By "substantially separated" is meant that at least 50 percent, preferably at least 75 percent, and more preferably at least 90 percent of the reactant having the smallest or limiting stoichiometrically reactable amount of reactant, as between the first and second reactant streams, has not become consumed by reaction by the point at which these gases have completed their axial transit of the recuperator (27). In this manner, the majority of the first reactant (30) is kept isolated from the majority of the second reactant (32), and the majority of the heat release from the reaction of combining reactants (30) and (32) will not take place until the reactants begin exiting the recuperator (27). Preferably the reactants are gases, but some reactants may comprise a liquid, mixture, or vapor phase.

The percent reaction for these regeneration streams is meant the percent of reaction that is possible based on the stoichiometry of the overall feed. For example, if gas (30) comprised 100 volumes of air (80 volumes N2 and 20 Volumes O2), and gas (32) comprised 10 volumes of Hydrogen, then the maximum stoichiometric reaction would be the combustion of 10 volumes of hydrogen (H2) with 5 volumes of Oxygen (O2) to make 10 volumes of H2O. In this case, if 10 volumes of Hydrogen were actually combusted in the recuperator zone (27), this would represent 100% reaction of the regeneration stream. This is despite the presence of residual un-reacted oxygen, because that un-reacted oxygen was present in amounts above the stoichiometric requirement. Thus, the hydrogen is the stoichiometrically limiting component. Using this definition, it is preferred than less than 50% reaction, more preferred than less than 25% reaction, and most preferred that less than 10% reaction of the regeneration streams occur during the axial transit of the recuperator (27).

In a preferred embodiment, the channels (28) and (33) comprise materials that provide adequate heat transfer capacity to create the temperature profiles (4) and (8) illustrated in FIG. 1 at the space velocity conditions of operation. Adequate heat transfer rate is characterized by a heat transfer parameter ATHT, below about 500° C., more preferably below about 100° C. and most preferably below about 50° C. The parameter ATHT, as used herein, is the ratio of the bed-average volumetric heat transfer rate that is needed for recuperation, to the volumetric heat transfer coefficient of the bed, hv. The volumetric heat transfer rate (e.g. cal/cm$^3$ sec) that is sufficient for recuperation is calculated as the product of the gas flow rate (e.g. gm/sec) with the gas heat capacity (e.g. ca./gm ° C.) and desired end-to-end temperature change (excluding any reaction, e.g. ° C.), and then this quantity divided by the volume (e.g. cm$^3$) of the recuperator zone (27) traversed by the gas. The ATHT in channel (28) is computed using gas (30), channel (33) with gas (32), and total recuperator zone (27) with total gas. The volumetric heat transfer coefficient of the bed, hv, is typically calculated as the product of a area-based coefficient (e.g. cal/cm2s° C.) and a specific surface area for heat transfer (av, e.g. cm2/cm$^3$), often referred to as the wetted area of the packing.

In a preferred embodiment, channels (28) and (33) comprise ceramic (including zirconia), alumina, or other refractory material capable of withstanding temperatures exceeding 1200° C., more preferably 1500° C., and still more preferably 1700° C. Materials having a working temperature of up to and in excess of 2000° C. might be preferred where there is concern with reaching the bed reaction adiabatic maximum temperature for sustained periods of time, to prevent reactor bed damage, provided the project economics and conditions otherwise permit use of such materials. In a preferred embodiment, channels (28) and (33) have wetted area between 50 ft-1 and 3000 ft-1, more preferably between 100 ft-1 and 2500 ft-1, and most preferably between 200 ft-1 and 2000 ft-1. Most preferably, channel means (28) comprise a ceramic honeycomb, having channels running the axial length of the recuperator reactor (27).

Referring again briefly to FIGS. 1(*a*) and 1(*b*), the inventive reactor system includes a first reactor (7) containing a first end (9) and a second end (11), and a second reactor (1) containing a primary end (3) and a secondary end (5). The embodiments illustrated in FIGS. 1(*a*), 1(*b*), and 2 are merely simple illustrations provided for explanatory purposes only and are not intended to represent a comprehensive embodiment. Reference made to an "end" of a reactor merely refers to a distal portion of the reactor with respect to an axial mid-point of the reactor. Thus, to say that a gas enters or exits an "end" of the reactor, such as end (9), means merely that the gas may enter or exit substantially at any of the various points along an axis between the respective end face of the reactor and a mid-point of the reactor, but more preferably closer to the end face than to the mid-point. Thereby, one or both of the first and second reactant gases could enter at the respective end face, while the other is supplied to that respective end of the reactor through slots or ports in the circumferential or perimeter out surface on the respective end of the reactor, such as illustrated in FIG. 6.

Figure 6:
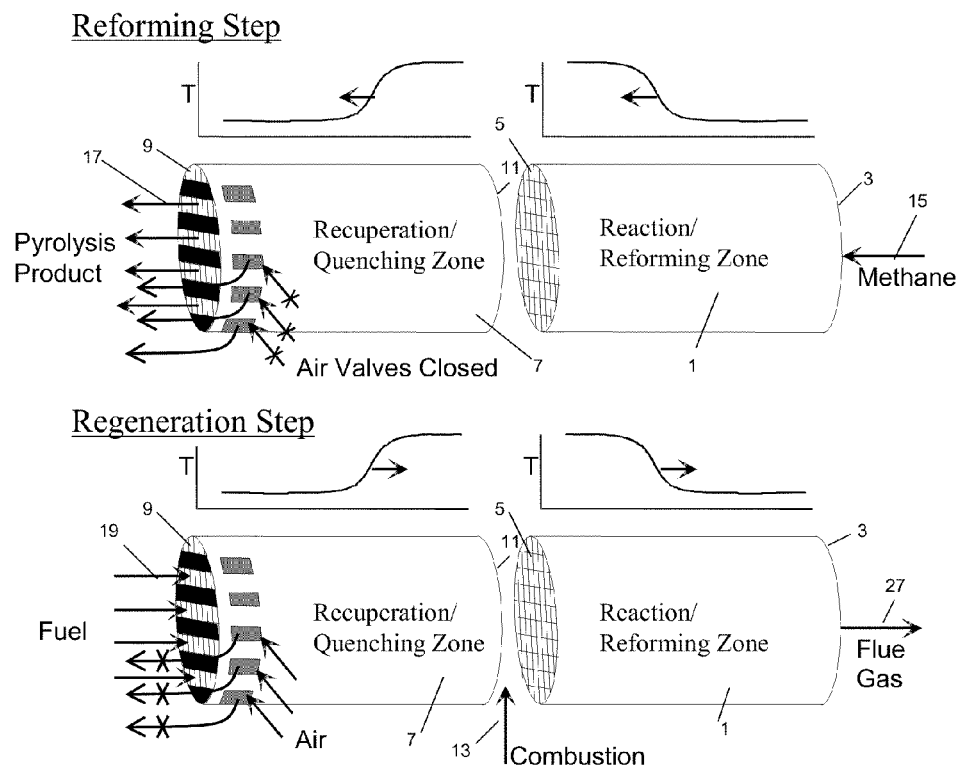
FIG. 6 illustrates yet another exemplary embodiment of a reactor system that utilizes separated, alternating layers of reactor bedding.

For example, in one embodiment, the channel segments could comprise horizontal layers, (e.g., like a stack of pancakes) within a generally rectangular box-like (not shown) or cylindrical-shaped first reactor, such as illustrated in FIG. 6, wherein each alternating layer conveys one of a first or second reactant while the two adjacent layers convey the other reactant. The embodiment of FIG. 6 illustrates an exemplary reactor system concept, wherein the first reactor comprises at least two layers of reactor bed material and the first channel comprises at least one of the at least two layers and the second channel comprises another of the at least two layers. Thus, every other layer may contain a feed port in the respective outer surface of the reactor, near the respective end of the reactor, to feed a reactant gas into the respective layers, while alternating layers are fed substantially simultaneously through the end face and/or by separate outer surface ports. A reactant flow path through each of the at least two layers is substantially not in fluid communication with a flow path through an immediately adjacent layer. A reactant flow path may preferably include one or more monoliths, having a plurality of conduits, the aggregate of which conduct one of the first or the second reactant through the first reactor, without permitting a substantial amount of cross flow to and adjacent flow path. Some cross flow might be permitted to occur in some embodiments, provided the total amount of cross flow and resulting early reaction does not appreciably alter the acceptable heat balance in the system. Thereby, a majority of the stoichiometrically available first and second reactants are available to react in the mixer (when present) and second reactor. FIG. 6 illustrates in simple form, how valves can be used to regulate flow through each of the layers of the first and second reactors during each half of the full reaction cycle. In one set of layers for supplying a common reactant, the side entry ports preferably provide entry for one reactant (e.g., air or fuel) that is isolated from entry of the other reactant. Valves can control flow of one reactant into (and out of) the side ports to alternate between "open" in the regeneration cycle and "closed" in the quenching cycle. When the first reactor is flowing reactant into the side ports for regeneration, other valves or lines leading from the respective ports/layers can close to prevent loss of the reactant. When the reactor is flowing generated acetylene gas from the reactor, these latter side port valves can open, while the reactant supply valves close, to permit flow of the generated acetylene-containing gas through all layers of the reactor. Although the illustrated exemplary embodiment of FIG. 6 includes side ports, the material entering through such ports is merely entering to gain access to the first end of the first reactor and does not expose the inlet components to the heat bubble in the reactor core.

As an alternative to using only the side port valves to flow reactant from the side port layers, the first end (end-cap) of the reactor may be provided with a set of flow restrictors on alternating layers, e.g., such as single pane louvers, like a check-valve, or a double-pane "duck-bill" type of louver, that can act as a flow restrictor or valve to prohibit flow of the other reactant into the side port containing layers from the end cap during regeneration, while permitting acetylene gas to flow through the side port layers and into the end cap plenum area or out of the side ports while the reactor is quenching the generated acetylene. Flow restrictors may be positioned on an end face (9) to cover or seal over at least a portion of the conduits, such as every other layer. The flow restrictors can close to permit flow into the conduits of one or more of the layers from the end face, during regeneration, and then open to permit flow through those layers during reformation stage. During the regeneration stage, so long as the pressure on the end-face of the first reactor is higher than the pressure in the side port layers within the reactor, the side port gas can flow through the reactor without flowing out of the end-face, while the other reactant maintains the louvers/flow restrictor in closed position to restrict or prevent flow of the other reactant into the side port layers. The process may thereby include a step of actuating at least one of a valve and/or a flow restrictor, such as a check valve, an actuated valve (e.g., electric, pneumatic, hydraulic, etc.) to prevent the undesirable flow of the restricted first or second reactant into the improper layer or portion of the reactor. The restrictor may open or close in response to pressure and pressure changes within the first portion/layers and second portion/layers of the reactor. Preferably, the flow restrictor(s) is passively responsive to pressure changes within the system, such as use of a hinge system. Thereby, the first reactor can utilize substantially the whole reactor bed and both of the first and second reactants to cool the quenching reactor and for heating the first and second reactants prior to their combining and reacting.

Figure 3:
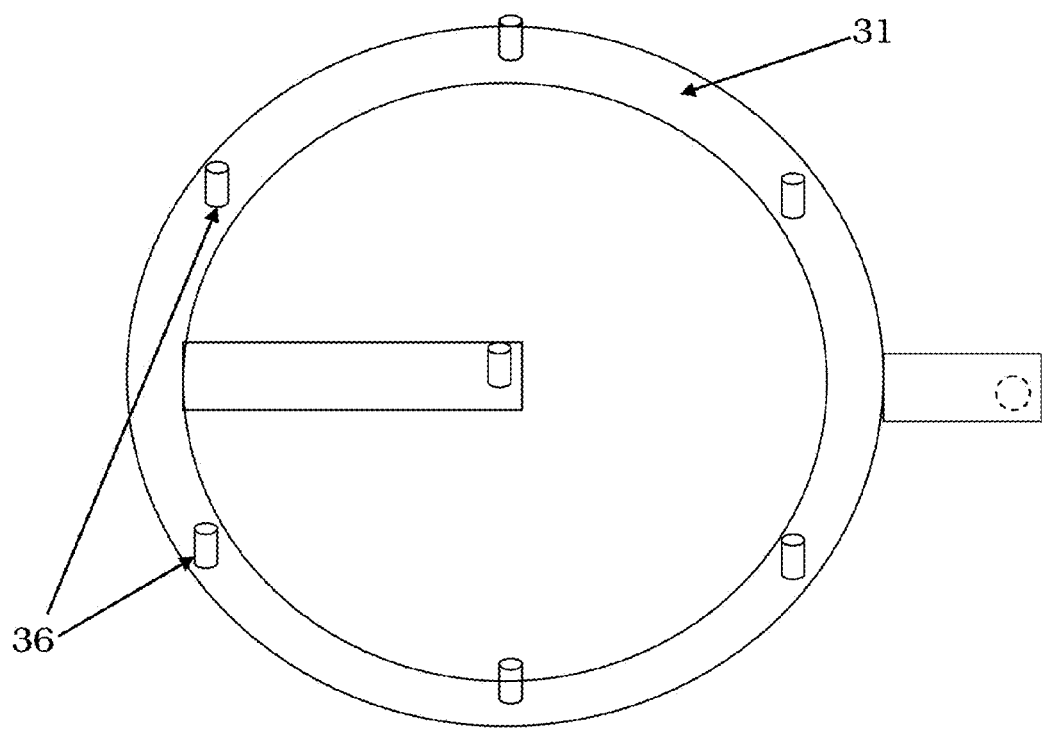
FIG. 3 illustrates an axial view of an exemplary gas distributor.

With regard to the various exemplified embodiments, FIG. 3 illustrates an axial view of an exemplary gas distributor (31) having apertures (36). Referring to both FIGS. 2 and 3, apertures (36) may direct the second reactant gas (32) preferentially to select channels (33). In a preferred embodiment, apertures (36) are aligned with, but are not sealed to, the openings/apertures of select channels (33). Nozzles or injectors (not shown) may be added to the apertures (36) that are suitably designed to direct the flow of the second gas (32) preferentially into the select channels (33). By not "sealing" the gas distributor apertures (36) (or nozzles/injectors) to the select channels (33), these channels may be utilized during the reverse flow or reaction cycle, increasing the overall efficiency of the system. Such "open" gas distributor (31) may be preferred for many applications, over a "closed" system, to facilitate adaptation to multiple reactor systems, such as where the reactor/recuperator beds may rotate or otherwise move in relation to the location of the gas stream for processing, e.g., such as with a rotating bed type reactor system.

When a gas distributor nozzle or aperture (36) in an "open" system directs a stream of reactant gas (32) toward the associated inlet channel and associated conduits in the reactor (preferably a honeycomb monolith(s)), the contents of that stream of reactant gas (32) will typically occupy a large number of honeycomb conduits (33) as it traverses the recuperator. This outcome is a geometric result of the size of the reactor segments and/or aperture size, relative to the size of the monolith honeycomb conduits. The honeycomb conduits occupied by gas (32) may, according to a preferred embodiment, be characterized as a bundle of conduits, typically oriented along the same axis as the aperture (36) and its issuing stream of gas (32). Conduits located near the center of this bundle/channel will contain a high purity of gas (32) and thus will likely not support exothermic reaction. Conduits located near the outer edge of the bundle will be in close proximity to conduits (28) carrying the other reactant. In an "open" system as described above, some mixing of the first gas (30) and the second gas (32) will be unavoidable near the peripheral edges of each stream of gas (32) that issues from the apertures (36). Thus, some conduits (28) and (33) near the outer edge of the bundle will carry some amount of both the first gas (30) and the second gas (32). Reaction or combustion between gases (30) and (32) could happen in these conduits before the gases completely traverse recuperator (27). Such gases would still be considered to be substantially separated, as long as the resulting reaction of the regeneration streams within the recuperator (27) is less than 50%, preferably less than 25%, and most preferably less than 10% of the stoichiometrically reactive reactant having the smallest or reaction limiting presence.

In some alternative embodiments, the recuperator reactor (27) may include, for example, packed bed or foam monolith materials (not shown) that permit more mixing or dispersion of reactants before fully traversing the first reactor. In this case, additional reaction may occur in the recuperator (27) due to mixing within the recuperator that is due to the axial dispersion of gases (30) and (32) as they pass though. This may still be an acceptable arrangement as long as the mixing and subsequent reaction of the regeneration streams within the recuperator (27) is less than 50%, preferably than less than 25%, and most preferably less than 10%. Methods for calculation of radial dispersion and mixing in bed media is known in the art.

During regeneration, the first gas (30) and second gas (32) transit the recuperator zone (27) via channels (28) and (33). It is a key aspect of this invention that heat, stored in the recuperator zone from the previous quench cycle, is transferred to both the first and second gases during the regeneration cycle. The heated gases are then introduced into mixer (44). The gas mixer (44), located between the recuperator (27) and the reactor (21), functions to mix the regenerating reaction gas streams (30) and (32), preferably at or near the interface of the reaction zone (21) and the mixer (44).

The mixer (44) is preferably constructed or fabricated of a material able to withstand the high temperatures expected to be experienced in the reaction zone during methane reforming at high selectivity and high conversion rates (>50 wt %). In a preferred embodiment, mixer (44) is constructed from a material able to withstand temperatures exceeding 1200° C., more preferably 1500° C., and most preferably 1700° C. In a preferred embodiment, mixer means (34) is constructed of ceramic material(s) such as alumina or silicon carbide for example.

FIG. 4 illustrates an axial view of one configuration of the mixer (44), together with a cut-away view FIG. 4a, of one exemplary embodiment of swirl-type mixer (47). The exemplary mixer (44) comprises mixer segments (45) having swirl mixer (47) located within the sections (45). In a preferred embodiment, mixer segments (45) are substantially equal in cross sectional area and the swirl mixers (47) are generally centrally located within the sections (45). Mixer segments (45) are positioned with respect to the reactor system to segment the gas flow of a plurality of gas channels (28) and (33). In a preferred embodiment, segments (45) may each have substantially equal cross sectional area to facilitate intercepting gas flow from a substantially equal number of gas channel means (28) and (33). Also in a preferred embodiment, the gas channels (28) and (33) are distributed within recuperator reactor (27) such that each of the segments (45) intercepts gas flow from a substantially equal fraction of both first gas channel means (28) and second gas channel means (33). Expressed mathematically, one can define fAi as the fraction of total cross sectional area encompassed by section i, f28i as the fraction of total channel means (28) intercepted by section i, and f33i as the fraction of total channel means (33) intercepted by section i. In a preferred embodiment, for each section i, the values f28i, and f33i will be within about 20% of (i.e. between about 0.8 and 1.2 times) the value of fAi, and more preferably within about 10%. One can further define f30i as the fraction of gas stream (30) intercepted by section i, and f32i as the fraction of gas stream (32) intercepted by the section i. In a more preferred embodiment, for each section i, the values of f30i, and f32i will be within about 20% of fAi, and more preferably within about 10%.

FIG. 4a illustrates an exemplary cut out section of an individual gas mixer segment (45) with swirl mixer (47). While the present invention may utilize a gas mixer known to the skilled artisan to combine gases from the plurality of gas channel means (28) and (33), a preferred embodiment of this invention minimizes open volume of the gas mixer (44) while maintaining sufficient mixing and distribution of the mixed gases. The term open volume means the total volume of the swirl mixers (47) and gas mixer segment (45), less the volume of the material structure of the gas mixer. Accordingly, gas mixer segment (45) and swirl mixer (47) are preferably configured to minimize open volume while concurrently functioning to provide substantial gas mixing of the gases exiting gas channels (28) and (33). In a preferred practice of the invention, gas mixer segment (45) dimensions L and D, are tailored to achieve sufficient mixing and distribution of gases (31) and (32) while minimizing open volume. Dimension ratio L/D is preferably in the range of 0.1 to 5.0, and more preferably in the range of 0.3 to 2.5. For general segments of area A, a characteristic diameter D can be computed as $2(A/\pi)^{1/2}$.

In addition, the total volume attributable to the gas mixer (44) is preferably tailored relative to the total volume of the first reactor bed (27) and reforming bed (21). Gas mixer (44) preferably has a total volume of less than about 20%, and more preferably less than 10% of the combined volume of the recuperator zone (27), the reformation zone (21), and the gas mixer (44).

Referring again to FIG. 2, the mixer (44) as configured combines gases from channels (33) and (28), and redistributes the combined gas across and into reaction zone (21). In a preferred embodiment, first reactant and second reactant are each a gas and one comprises a fuel and the other an oxidant. Fuel may comprise hydrogen, carbon monoxide, hydrocarbons, oxygenates, petrochemical streams, or mixtures thereof. Oxidant typically comprises a gas containing oxygen, commonly mixed with N2, such as air. Upon mixing, the fuel and oxidant at mixer (44), the gases combust, with a substantial proportion of the combustion occurring proximate to the entrance of the reaction zone (21).

The combustion of the fuel and oxygen-containing gas proximate to the entrance of the reformer or reaction zone (21) creates a hot flue gas that heats (or re-heats) the reaction zone (21) as the flue gas travels across that zone. The composition of the oxygen-containing gas/fuel mixture is adjusted to provide the desired temperature of the reaction zone. The composition and hence reaction temperature may be controlled by adjusting the proportion of combustible to non-combustible components in the mixture. For example, non-combustible gases or other fluids such as H2O, CO2, and N2 also may be added to the reactant mixture to reduce combustion temperature. In one preferred embodiment, non-combustible gases comprise steam, flue gas, or oxygen-depleted air as at least one component of the mixture.

Referring again to regeneration FIG. 1(b), the reacted, hot combustion product passes through reformer (1), from the secondary end (5) to the primary end (3), before being exhausted via conduit (18). The flow of combustion product establishes a temperature gradient, such as illustrated generally by example graph (8), within the reformation zone, which gradient moves axially through the reformation reaction zone. At the beginning of the regeneration step, this outlet temperature may preferably have an initial value substantially equal (typically within 25° C.) to the inlet temperature of the reforming feed of the preceding, reforming, step. As the regeneration step proceeds, this outlet temperature will increase somewhat as the temperature profile moves toward the outlet, and may end up 50 to 200° C. above the initial outlet temperature.

The inventive processes and apparatus has been described generally and with regard to illustrative embodiments, such as provided within the accompanying figures. The invention has overcome the limitations that rendered the prior art impractical and non-useful for practicing methane reforming to acetylene. The following text elaborates on the previous discussion and discloses some preferred embodiments of the methods and apparatus for practicing the invention.

Referring again to FIGS. 1(a) and 1(b), the invention includes a preferred process for the manufacture of acetylene from methane feed using a reverse-flow reactor system, wherein the reactor system includes (i) a first reactor (7) comprising a first end (9) and a second end (11), and (ii) a second reactor (1) comprising primary end (3) and a secondary end (5), the first and second reactors oriented in a series relationship with respect to each other such that the secondary end of the second reactor is proximate the second end of the first reactor, the process comprising the steps of: (a) supplying a first reactant through a first channel in the first reactor and supplying at least a second reactant through a second channel in the first reactor, such that the first and second reactants are supplied, such as via conduit (19) to the first reactor from the first end of the first reactor; (b) combining the first and second reactants at the second end of the first reactor and reacting the combined reactants to exothermically produce a heated reaction product; (c) passing the heated reaction product through the second reactor (1) to transfer heat from the reaction product to the second reactor; (d) thereafter supplying methane through the heated second reactor to the first reactor, such as via conduit (15) to convert at least a portion of the methane into acetylene; (e) passing the supplied methane and the produced acetylene through the first reactor to quench the methane and the produced acetylene; and (f) recovering the produced acetylene, such as via conduit (17). The first and second reactors are oriented in a series relationship with respect to each other means that the reactors are in series with respect to a common flow path, such that material exiting from one of the reactors flows into the other reactor, regardless of direction of flow. There may also be space or components intermediate the first and second reactors, such as a mixer. The secondary end of the second reactor is proximate the second end of the first reactor is provided merely for orientation reference. Flow of material exiting the second end of the first reactor follows the flow path to enter the secondary end of the second reactor, and vice versa. Preferably, the flow path through the reactors share a common axis but the reactors may be arranged otherwise, such as beside each other with the flow path generally forming a "U" shape. Also, the spacing between the reactors is subject to adjustment as determined by the presence of mixers or other apparatus, but it may be preferred that they are closer together as opposed to more distant between them, such that the reaction products may move quickly between the reactors.

Preferably, the cyclic reverse flow reactor system further comprises a mixer (not shown in FIG. 1, but illustrated in FIG. 2 as component (44)) situated intermediate (13) the first reactor and second reactor to mix the first reactant with the second reactant and more preferably, the first channel and the second channel axially traverse the first reactor to pass the first and second reactants to the mixer; and further, that the first and second reactants are combined at the second end of the first reactor such that less than half of the total weight of the combined first and second reactant supplied, based upon the total weight of the first and second reactant, is reacted exothermically before the supplied first and second reactants exit the second end of the first reactor.

The preferred process may also include the optional step of supplying hydrogen in the second reactor to moderate the reaction of the methane. The supplied hydrogen may be as hydrogen gas, a mixture of gases comprising hydrogen, steam, or another product that provides or yields hydrogen in the reactor. The hydrogen may be mixed with the methane so that the mixture is introduced into the reforming reactor, or each of the methane and hydrogen gas may separately be introduced into the reformer. In a preferred embodiment, hydrogen is mixed with the methane before introduction into the reactor. Preferred molar ratio of hydrogen to methane is between 0 and 5. More preferred ratio of hydrogen to methane in the present invention is between about 1 and about 3.

The first and second regeneration reactants may exothermically react in at least one of (i) the second end of the first reactor, such as at least partially within a second end of the recuperator, (ii) a region intermediate the first and second reactors, such as within a mixer or space between the first and second reactors, and (iii) the secondary end of the second reactor, such as at least partially within a secondary end of the reformer reactor, including at an interface zone between a reformer side of the mixer and the reformer reactor. Preferably, the region (13) intermediate the first and second reactors includes a mixer for mixing and combusting at least a portion of the first and second reactants.

It may also be preferred in some embodiments that, in step (b) above, the first and second reactants are combined in a mixer (44) positioned proximate the second end of the first reactor, wherein at least about 75% of the regeneration stream is reacted. Thus, up to about 25 wt % of the combined regeneration stream may have combusted or reacted substantially within the first reactor, preferably nearer the second end of the first reactor than the first end. This leaves about 75 wt % to react to provide heat to the mixer and reformer/second reactor (1). In some alternative embodiments, up to 50 weight percent of the combined reactants may be permitted to react before leaving the first reactor. In a most preferred embodiment, 90% of the regeneration stream is reacted in the mixer or in a region of reformer (21) proximate to the mixer (near the second end, near end (5) in FIG. 1b).

For those embodiments comprising a mixer, the mixer should be constructed from material able to withstand temperatures in excess of about 1200° C., preferable to withstand temperatures in excess of about 1500° C., and most preferably to withstand temperatures in excess of about 1700° C. In some preferred embodiments, the mixer comprises a refractory material, such as a ceramic. In a preferred embodiment, the first reactor or regenerator (7) has a geometric void volume A, and the second reactor (1), has a geometric void volume B, and the mixer (44) (including void volume (13) for the embodiments not having a mixer device but instead merely providing a region for the gases to comingle, mix, and combust) has a geometric void volume C, whereby void volume C is less than or equal to about 20 percent and preferably less than or equal to about 10 percent, of the total combined void volumes A plus B plus C. The term geometric void is used herein to denote the void volume in major passages that gases use to transit the reactor, and to exclude volumes than may be present in small pores within the walls of the reactor contents. For example, for honeycomb monoliths, geometric volume includes the volume in the channels, but excludes any pore volume that may exist in the channel walls.

Preferably, the first reactant used in the exothermic regenerative reaction includes a fuel comprising CO, H2, hydrocarbon(s), oxygenates, petrochemicals, or a mixture thereof. Other components, reactive and/or non-reactive, may also be present in the fuel. The second reactant may comprise oxygen, such as from air. In the reforming step, the supplied methane may also be supplied from the primary end of the second reactor to act as a diluent or to react with the methane in the second reactor.

According to some preferred processes, the step of supplying the methane feed through the second reactor is performed at a pressure in the second reactor of from about 5 psia up to about 45 psia, or more preferably at a pressure in the second reactor of from about 15 psia up to about 35 psia. The regeneration step of supplying at least one of the first reactant and the second reactant to the first reactor may be performed at a relatively low pressure, such as about the pressure that the step of reforming is performed. Alternatively, such as in an embodiment where the regeneration step is supplied a regeneration reactant including fuel and/or the exhaust gas from a turbine, compressor, or blower, the regeneration step may be performed at a pressure great than about 35 psia, such as a pressure of preferably up to about 250 psia. A larger pressure may be utilized. However equipment and process considerations may make use of such pressures undesirable. Preferably, the heated reaction product in the regeneration step heats at least a portion of the second reactor, preferably the secondary end (5) of the second reactor (1), to a temperature of at least about 1500° C., and more preferably to a temperature of at least about 1600° C.

Reactor system cycle time includes the time spent at regeneration plus the time spent at reforming, plus the time required to switch between regeneration and reformation and vice versa. Thus, a half cycle may be the substantially the time spent only on regeneration, or the time spend on reformation. A complete cycle includes heating the bed, feeding the methane, and quenching the acetylene containing reaction product. Typical cycle times for preferred embodiments utilizing honeycomb monoliths may be between 1 second and 240 seconds, although longer times may be desired in some alternative embodiments. More preferably for the preferred monolith embodiments, cycle times may be between 2 seconds and 60 seconds. It is not necessary that the regeneration and reformation steps to have equal times, and in a well-refined application it is likely that these two times will not be equal.

Also, although not required for reforming methane to acetylene, in some alternative embodiments, the reforming/second reactor (1) may further comprise a reaction catalyst. After the methane has been reformed and passed through the quenching first reactor (7), the process may also include the step of recovering the acetylene from the quenched acetylene-methane mixture. Such recovery processes may also include the step(s) of recovering at least one of hydrogen and methane from the quenched acetylene-methane mixture for recycling to the second reactor.

In a broad aspect, the inventive process includes a process for the pyrolysis manufacture of acetylene, comprising the steps of: (a) supplying a first reactant through a first portion of a reactor bed; (b) supplying at least a second reactant through a second portion of the reactor bed substantially separate from the first portion of the reactor bed, and (c) combining the supplied first reactant with the second reactant after the first and second reactants have separately traversed at least a portion of the reactor bed, for the first and second reactants to exothermically react with each other; wherein both of the first and second portions of the reactor bed are utilized to quench a synthesized reaction product comprising acetylene, after the combined first and second reactants have reacted with each other. Preferably the synthesized reaction product is a product of pyrolysis of a feed that includes methane. According to other embodiments, the synthesized reaction product is a product of pyrolysis of a feed that includes hydrocarbons other than methane, such as ethane, propane, naphtha, or other pyrolyzable hydrocarbons, and/or feeds that include methane as a component therein. Although the present invention pertains primarily to inventive processes, methods, and equipment for converting methane to acetylene, the subject processes and equipment may also be utilized for pyrolysis of feeds other than methane, including liquid and/or gas feeds, into any of a number of desirable pyrolysis reaction products.

The invention also includes the reactor system equipment and apparatus utilized in performing the inventive processes. According to one preferred embodiment, the subject invention includes a cyclic reverse flow reactor for the manufacture of acetylene from methane feed, wherein the reactor includes a reactor system that comprises: (i) a first reactor comprising a first end and a second end; (ii) a second reactor comprising primary end and a secondary end, the first and second reactors oriented in a series relationship with respect to each other such that the secondary end of the second reactor is proximate the second end of the first reactor; wherein the first reactor further comprises; (a) a first channel to supply at least a first reactant from the first end of the first reactor to the second end of the first reactor; (b) a second channel to supply at least a second reactant from the first end of the first reactor to the second end of the second reactor; and (c) a product removal line to remove at least one of methane and a produced acetylene from the first reactor; wherein the second reactor further comprises; (d) a flue gas removal line to remove at least a portion of the heated reaction product produced from mixing and reaction of the first and second reaction products; and (e) a methane feed line to feed methane to the primary end of the second reactor. Preferably, at least one of the first channel and the second channel prevent a stoichiometric reactable majority of the reaction limiting first reaction product and second reaction product, from exothermically reacting with each other to produce a reaction product until the unreacted first and second reaction products exit the second end of the first reactor, based upon the total combined weight of the first and second reaction products. Preferably, the reactor further comprises a mixer situated intermediate the first reactor and second reactor to mix the first reactant with the second reactant.

The preferred mixer may also further comprise one or more gas mixer segments, wherein each segment receives at least a portion of the first and second reactant to mix the at least a portion of the first and second reactant in the respective segment. In preferred embodiments, the mixer is constructed from material able to withstand temperatures in excess of about 1200° C., more preferably in excess of about 1500° C., still more preferably in excess of about 1700° C., and yet still more preferably in excess of about 2000° C. According to some embodiments, the mixer comprises a ceramic. Preferably the first reactor has a void volume A, and the second reactor has a void volume B, and the mixer has a void volume C, whereby void volume C is less than or equal to about fifty percent and more preferably less than or equal to about twenty percent of the total of void volume A plus void volume B plus volume C.

The reactor further comprises a methane/feed supply line to supply methane, and or any optional other gases, such as hydrogen/diluent/additional reactants, to the primary end of the second reactor for conversion to acetylene in the second reactor. The reactor may also include hydrogen diluent or reaction component (including a component that comprises hydrogen) supply line to supply hydrogen to the primary end of the second reactor so that the hydrogen can react with the methane. The reactor also includes a fuel gas supply line to supply a fuel gas to one of the first channel and the second channel in the first reactor, and a second reactant supply line to supply a second reactant to react with the first reactant. The second reactant preferably comprises oxygen and the second reactant may include air. The second reactant may also include at least one of (i) a noncombustible gas, and (ii) a mixture of combustible and noncombustible gases, such as an exhaust gas recycle (EGR).

Example 1

Figure 5:
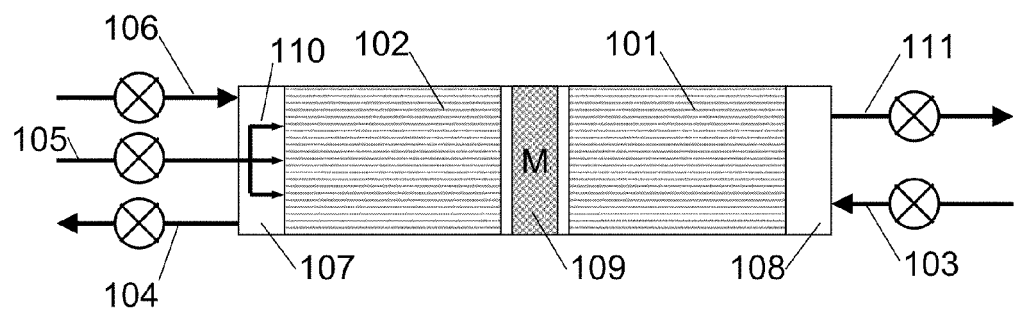
FIG. 5 illustrates another exemplary embodiment of a reactor system, including a mixer and some illustrative component piping.

The following example is merely illustrative of one exemplary embodiment and process, and is not intended to limit the scope of the invention. Methane is converted to acetylene in a pair of reactor systems, each arranged according to simplified illustration FIG. 5, suitably valved, such that one reactor system is executing the regeneration step while the other reactor system is executing the pyrolysis step. Some embodiments may also include more reactor systems than just a pair, such as multiple reactor systems, each operating in a phased timing arrangement, such that the entire process is substantially continuous. The reactor system includes at least a first reactor/recuperator (102), a mixer or mixing zone (109), and a second reactor/reforming zone (101).

Both reforming (101) and recuperation (102) reactor zones comprise extruded, ceramic honeycomb monolith blocks, stacked in 3 dimensions to fill the reactor zone volume. The overall reactor systems are about 10 ft in diameter and about 4 ft in height or axial length (excluding insulation and vessel shell that surrounds the reactor). Recuperation zone (102) is at the top, and measures about 10 ft in diameter by about 17 inches long. Mixer zone (109) is about 10 ft in diameter by about 4 inches long and reforming zone (101) is about 10 ft in diameter by about 27 inches long. The ceramic honeycomb monoliths have conduit structure characterized as having about 400 conduits or pores per square inch and 56% geometric void volume. The mixer zone is comprised of many individual mixer blocks, each block representing a mixer section (45) as described with respect to FIG. 4. Blocks are hexagonal in cross-section and measure 3 inches across the flats of the hexagon and 4 inches in height, and function to mix the regeneration fuel and oxidant reactants, and redistribute flow to the conduits in downstream zone. Individual mixer blocks are stacked side by side to fill the 10-ft diameter mixer zone (109).

During the regeneration step, regeneration oxidant (106) is fed into plenum (107) located above the recuperation zone (102). Regeneration fuel (105) is fed into a fuel distributing sparger or distributor (110) that is located within the plenum and which has one fuel orifice (such as aperture (36) in FIG. 3) positioned axially above each of the mixer block segments in the mixer zone (109), whereby each orifice feeds fuel into a group of conduits thus forming a fuel channel. Combustion product, or flue gas (111) resulting from the combustion of the regeneration fuel (105) and oxidant (106) is withdrawn from the plenum (108) that is below the reforming zone and that accesses the individual conduits in the reforming zone.

During the pyrolysis step, pyrolysis feed (103) is introduced into the reforming zone (101) by way of the manifold or plenum (108). If desired, a sparger or distributor (not shown) may also be used within the plenum (108) to supply the methane feed into the reformer (101). Pyrolysis feed is converted to acetylene as it travels through the reforming zone (101), the mixer zone (109) and the recuperator zone (102). Quenched pyrolysis product (104) is recovered from the plenum (107) above the recuperator zone (102).

The regeneration step and pyrolysis step are each operated for a selected duration, which for this Example is three seconds in each direction, before switching to the alternate step, such that the complete cycle requires about six seconds plus switching time. Composition and flow rate of the total streams are shown in Table 1, below, for the pair of reactor systems. These flows represent substantially continuous flows, as one reactor is always in pyrolysis while the other reactor is in regeneration stage. This example is somewhat idealized, because it provides no time to switch the reactor from one step to the next. More sophisticated cycles that provide for such switching may be added by one skilled in the art.

TABLE 1

| | Stream | | | | |
| --- | --- | --- | --- | --- | --- |
| | 103 | 104 | 105 | 106 | 111 |
| | | | T, ° C. | | |
| | 100 kg/hr | 354 kg/hr | 100 kg/hr | 100 kg/hr | 265 kg/hr |
| C3+ | | 476 | | | |
| C2H2 | | 21,740 | | | |
| C2H4 | | 2,162 | | | |
| C2H6 | | 81 | | | |
| CH4 | 47,032 | 14,795 | 2,436 | | |
| H2O | | | | | 29,485 |
| H2 | 11,696 | 17,670 | 2,630 | | |
| CO2 | | | | | 13,166 |
| N2 | | | | 229,028 | 229,042 |
| O2 | | | | 65,470 | 29,686 |
| Total | 58,728 | 56,924 | 5,066 | 294,498 | 301,379 |

This Example demonstrates the successful conversion of methane to acetylene and hydrogen, and supports the following conclusions: (1) High productivity of acetylene. The inventive reactor system can produce acetylene yields that are many times (e.g., >10 times) higher than prior art Wulff-type reactors. (2) The process and reactor system succeeds without use of metals or degradable components exposed to the hot zone. (3) High selectivity and yield is achieved on a commercial size reactor system, demonstrating that the inventive system is useful for high production rates, such as on a commercial scale.

Trade names used herein are indicated by a ™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The invention has been described above with reference to numerous embodiments and specific examples. Many variations will suggest themselves to those skilled in this art in light of the above detailed description. All such obvious variations are within the full intended scope of the appended claims.

What is claimed is:

1. A process for the pyrolysis manufacture of acetylene, comprising the steps of:
   (a) supplying a first reactant through a first portion of a reactor bed;
   (b) supplying at least a second reactant through a second portion of the reactor bed substantially separate from the first portion of the reactor bed; and
   (c) combining the supplied first reactant with the second reactant after the first and second reactants have separately traversed at least a portion of the reactor bed, for the first and second reactants to exothermically react with each other;
   wherein both of the first and second portions of the reactor bed are utilized to quench a pyrolysis reaction product comprising acetylene, after the combined first and second reactants have reacted with each other.

2. The process of claim 1, wherein the reaction product is a product of pyrolysis of a feed that includes methane.

3. The process of claim 1, wherein the synthesized reaction product is a product of pyrolysis of a feed that includes hydrocarbons other than methane.

4. The process of claim 1, wherein the first reactant is supplied through the reactor bed substantially simultaneously with the supplying of the at least a second reactant through the reactor bed.

* * * * *